US011058283B2

United States Patent
Miyazaki

(10) Patent No.: US 11,058,283 B2
(45) Date of Patent: Jul. 13, 2021

(54) ENDOSCOPE WHICH OUTPUTS AN OPTICAL IMAGE SIGNAL BASED ON AN ACQUIRED ELECTRICAL IMAGE SIGNAL, AND ENDOSCOPIC SYSTEM

(71) Applicant: OLYMPUS CORPORATION, Hachioji (JP)

(72) Inventor: Yasuhiro Miyazaki, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 382 days.

(21) Appl. No.: 15/982,493

(22) Filed: May 17, 2018

(65) Prior Publication Data

US 2018/0263470 A1 Sep. 20, 2018

Related U.S. Application Data

(63) Continuation of application No. PCT/JP2015/083607, filed on Nov. 30, 2015.

(51) Int. Cl.
*A61B 1/00* (2006.01)
*H04N 5/225* (2006.01)
*A61B 1/06* (2006.01)

(52) U.S. Cl.
CPC ...... *A61B 1/00096* (2013.01); *A61B 1/00006* (2013.01); *A61B 1/00013* (2013.01);
(Continued)

(58) Field of Classification Search
CPC ............ A61B 1/00009; A61B 1/00013; A61B 1/00165; A61B 1/05; A61B 1/07; H04N 5/2254; G02B 6/42
See application file for complete search history.

(56) References Cited

U.S. PATENT DOCUMENTS 6,343,171 B1 * 1/2002 Yoshimura ............... G02B 6/43
 385/50
6,458,078 B1 * 10/2002 Ludtke ............... A61B 1/00013
 348/E5.029
7,329,050 B1 * 2/2008 Dugan ................. G02B 6/3885
 385/44
(Continued)

FOREIGN PATENT DOCUMENTS

JP 63313970 12/1988
JP 2006181021 A 7/2006
(Continued)

OTHER PUBLICATIONS

International Preliminary Report on Patentability (IPRP) dated Feb. 23, 2016 issued in International Application No. PCT/JP2015/083607.
(Continued)

*Primary Examiner* — John P Leubecker
(74) *Attorney, Agent, or Firm* — Holtz, Holtz & Volek PC

(57) ABSTRACT

An endoscope includes: an insertion unit; an imaging unit to image a subject under examination and output an electrical image signal; a light modulation device to output an optical image signal based on the electrical image signal output from the imaging unit; a first light cable inserted in the insertion unit to transmit light emitted by a communication light source to the light modulation device; and a second light cable inserted in the insertion unit to transmit the optical image signal output from the light modulation device outside the insertion unit. The communication light source is different from an illumination light source emitting an illumination light for illuminating the subject under examination. The light modulation device modulates the light transmitted by the first light cable to generate the optical image signal.

16 Claims, 12 Drawing Sheets

(52) U.S. Cl.
CPC ........ *A61B 1/00126* (2013.01); *A61B 1/0676* (2013.01); *H04N 5/2256* (2013.01); *A61B 1/00009* (2013.01); *A61B 1/00045* (2013.01); *H04N 2005/2255* (2013.01)

(56) References Cited

U.S. PATENT DOCUMENTS

| | | | | |
|---|---|---|---|---|
| 8,241,205 B2* | 8/2012 | Mori | ........................ | A61B 1/04 600/109 |
| 2007/0165981 A1* | 7/2007 | Tanaka | .................... | G02B 6/327 385/33 |
| 2008/0118202 A1* | 5/2008 | Kato | ........................ | G02B 6/43 385/14 |
| 2010/0284545 A1* | 11/2010 | Dietz | ..................... | G09B 15/00 381/58 |
| 2011/0194803 A1* | 8/2011 | Shin | ...................... | G02F 1/2257 385/3 |
| 2011/0292194 A1* | 12/2011 | Kato | ...................... | A61B 1/045 348/65 |
| 2013/0096380 A1* | 4/2013 | Matsuzawa | ........ | A61B 1/00057 600/109 |
| 2013/0182099 A1* | 7/2013 | Nakamura | ............. | G02B 6/428 348/86 |
| 2015/0086162 A1* | 3/2015 | Miyahara | ........... | G02B 23/2446 385/33 |
| 2016/0029874 A1* | 2/2016 | Usami | .................... | A61B 1/045 600/110 |

FOREIGN PATENT DOCUMENTS

| | | |
|---|---|---|
| JP | 2008307148 A | 12/2008 |
| JP | 2009095554 A | 5/2009 |
| JP | 2015000173 A | 1/2015 |
| JP | 2015160098 A | 9/2015 |

OTHER PUBLICATIONS

International Search Report (ISR) dated Nov. 30, 2015 issued in International Application No. PCT/JP2015/083607.

* cited by examiner

ENDOSCOPE WHICH OUTPUTS AN OPTICAL IMAGE SIGNAL BASED ON AN ACQUIRED ELECTRICAL IMAGE SIGNAL, AND ENDOSCOPIC SYSTEM

CROSS-REFERENCE TO RELATED APPLICATIONS

This application is based upon and claims the benefit of priority from the prior International Patent Application No. PCT/JP2015/83607, filed Nov. 30, 2015, the entire contents of which are incorporated herein by reference.

BACKGROUND

1. Field of the Invention

The present invention relates to endoscopes and, more particularly, to an endoscope capable of optical transmission of an image signal.

2. Description of the Related Art

Endoscopic devices are widely used in the field of medicine to observe an organ of a subject such as a patient. In an endoscopic device, it is common to use a scheme of transmitting a video signal from an imaging device provided in a distal unit to a device outside the endoscope, maintaining the video signal as an analog electric signal.

The total length of an endoscope amounts to several meters so that an analog video signal tends to be affected by external noise during transmission, resulting in degradation in the image quality. In particular, noise of a level that could not occur in normal environments is abundant in medical practice sites where an endoscope is used due, for example, to devices such as electric scalpels being in operation. Therefore, the transmission is heavily affected by noise.

In order to address the impact of noise like this, there is proposed an endoscopic device adapted to convert an electric signal from an imaging device into an optical signal before transmitting it to the image processing device. For example, a light modulation unit may be provided in the distal unit of an endoscope and the optical signal generated by light emission in the light modulation unit is transmitted to the image processing device via a light transmission cable.

SUMMARY

Recently, use of high-resolution imaging devices has been studied to enable clearer image observation. In this case, the amount of information of the image signal that should be transmitted increases so that it is required to increase the speed of the transmission channel. Higher speed of light modulation and higher outputs are useful to realize high-speed light transmission. However, this accompanies an increase in power consumption in the light modulation unit and an impact of heat generation. The distal unit of an endoscope is inserted into a subject such as a patient. It is therefore desired to realize high-speed light transmission and restrict the amount of heat generation at the distal unit at the same time.

The present invention has been made in view of these situations, and an illustrative purpose of an embodiment is to provide an endoscope of an optical transmission scheme in which an impact of heat in the distal unit is reduced.

The endoscope according to an embodiment of the present invention includes: an insertion unit including a distal unit oriented toward a subject under examination; an imaging unit provided in the distal unit to image the subject under examination and output an electrical image signal; a light modulation device provided in the distal unit to output an optical image signal based on the electrical image signal output from the imaging unit; a first light cable inserted in the insertion unit to transmit light emitted by a communication light source provided outside the distal unit to the light modulation device; and a second light cable inserted in the insertion unit to transmit the optical image signal output from the light modulation device outside the insertion unit. The communication light source is different from an illumination light source emitting an illumination light for illuminating the subject under examination, and the light modulation device modulates the light transmitted by the first light cable to generate the optical image signal.

Another embodiment of the present invention relates to an endoscopic system. The endoscopic system includes an endoscope and an image processing device for processing an optical image signal from the endoscope. The endoscope includes: an insertion unit including a distal unit oriented toward a subject under examination; an imaging unit provided in the distal unit to image the subject under examination and output an electrical image signal; a light modulation device provided in the distal unit to output an optical image signal based on the electrical image signal output from the imaging unit; a first light cable inserted in the insertion unit to transmit light emitted by a communication light source provided outside the distal unit to the light modulation device; and a second light cable inserted in the insertion unit to transmit the optical image signal output from the light modulation device outside the insertion unit. The communication light source is different from an illumination light source emitting an illumination light for illuminating the subject under examination, the light modulation device modulates the light transmitted by the first light cable to generate the optical image signal, and the image processing device generates an image capturing the subject under examination by demodulating the optical image signal transmitted by the second light cable.

Optional combinations of the aforementioned constituting elements, and implementations of the invention in the form of methods, apparatuses, and systems may also be practiced as additional modes of the present invention.

BRIEF DESCRIPTION OF THE DRAWINGS

Embodiments will now be described, by way of example only, with reference to the accompanying drawings that are meant to be exemplary, not limiting, and wherein like elements are numbered alike in several figures, in which.

DETAILED DESCRIPTION

Figure 1:
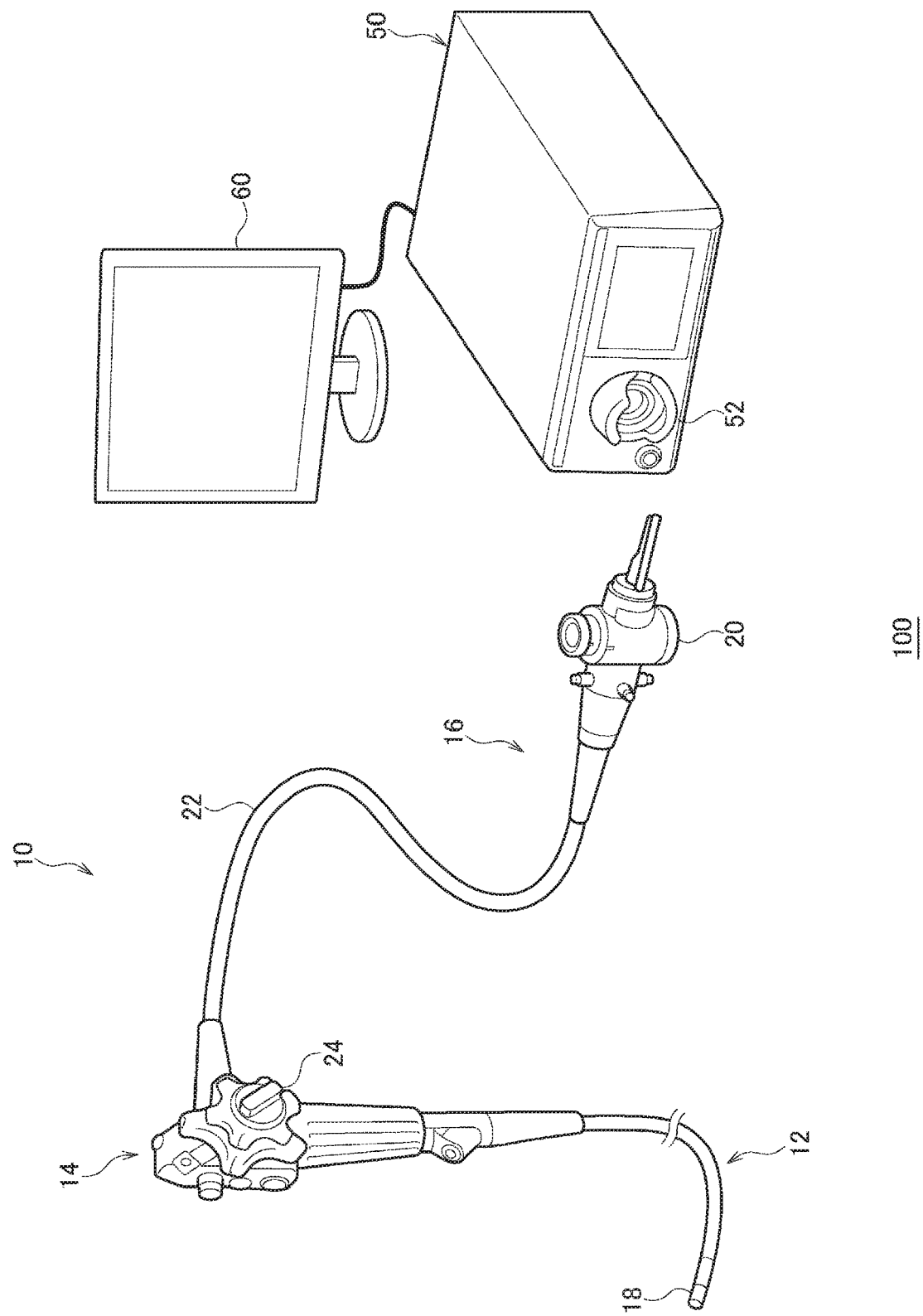
FIG. 1 schematically shows a configuration of an endoscopic system according to an embodiment.

The invention will now be described by reference to the preferred embodiments. This does not intend to limit the scope of the present invention but to exemplify the invention.

First, some of the embodiments according to the invention will be summarized. An embodiment of the present invention relates to an endoscope. The endoscope comprises: an insertion unit including a distal unit oriented toward a subject under examination; an imaging unit provided in the distal unit to image the subject under examination and output an electrical image signal; a light modulation device provided in the distal unit to output an optical image signal based on the electrical image signal output from the imaging unit; a first light cable inserted in the insertion unit to transmit light emitted by a communication light source provided outside the distal unit to the light modulation device; and a second light cable inserted in the insertion unit to transmit the optical image signal output from the light modulation device outside the insertion unit. The communication light source is different from an illumination light source emitting an illumination light for illuminating the subject under examination, and the light modulation device modulates the light transmitted by the first light cable to generate the optical image signal.

According to this embodiment, the communication light source is outside the distal unit of the endoscope. It is therefore possible to reduce the impact of heat generation in the distal unit even when a high-output communication light source is used. By using the communication light source that is separate from the illumination light source, optical transmission of a higher quality is realized.

The endoscope may further comprise an endoscope user operation unit connected to the insertion unit. The communication light source may be provided in the endoscope user operation unit. According to this embodiment, the communication light source is provided in the endoscope user operation unit that is not inserted into the subject such as a patient. Therefore, the impact of heat generation from the communication light source on the subject is restricted.

The endoscope may further comprise a light source controller provided in the endoscope user operation unit to control an output of the communication light source. The light source controller may control the output of the communication light source based on a light emission intensity of the communication light source.

The endoscope may further comprise an endoscope user operation unit connected to the insertion unit, a connection unit connectable to an image processing device for processing the optical image signal; and a light source controller for controlling an output of the communication light source. At least a portion of a set of the communication light source and the light source controller may be provided in the connection unit, and the light source controller may control the output of the communication light source based on a light emission intensity of the communication light source.

The light source controller may control the output of the communication light source based on a light intensity of the optical image signal transmitted by the second light cable.

The endoscope may further comprise a light splitter that branches a transmission channel of the optical image signal. The light source controller may include a sensing unit for sensing the light intensity of the optical image signal branched by the light splitter and control the output of the communication light source in accordance with a value sensed by the sensing unit.

The light splitter and the light source controller may be arranged on the same substrate and provided in the endoscope user operation unit.

The endoscope may further comprise a third light cable inserted in the insertion unit to transmit the optical image signal output from the light modulation device to the light source controller. The optical image signal transmitted by the second light cable may be transmitted outside the endoscope, and the light source controller may control the output of the communication light source in accordance with a light intensity of the optical image signal transmitted by the third light cable.

The communication light source may be a semiconductor laser, and the first light cable and the second light cable may be a single mode optical fiber.

The endoscope may comprise a plurality of light modulation devices. The second light cable may be a multicore fiber capable of transmitting optical image signals output from the plurality of light modulation devices.

At least one of the second light cable and the third light cable may be a multimode optical fiber.

The communication light source may emit one or a plurality of single-wavelength light beams.

The endoscope may further comprise a connection unit connectable to an image processing device for processing the optical image signal. The second light cable in the connection unit may have a convex-shaped fiber outgoing end from which the optical image signal outgoes.

The communication light source may emit light included in a wavelength band of 1200 nm-1400 nm.

Another embodiment of the present invention relates to an endoscopic system. The endoscopic system comprises an endoscope and an image processing device for processing an optical image signal from the endoscope. The endoscope includes: an insertion unit including a distal unit oriented toward a subject under examination; an imaging unit provided in the distal unit to image the subject under examination and output an electrical image signal; a light modulation device provided in the distal unit to output an optical image signal based on the electrical image signal output from the imaging unit; a first light cable inserted in the insertion unit to transmit light emitted by a communication light source provided outside the distal unit to the light modulation device; and a second light cable inserted in the insertion unit to transmit the optical image signal output from the light modulation device outside the insertion unit. The communication light source is different from an illumination light source emitting an illumination light for illuminating the subject under examination, the light modulation device modulates the light transmitted by the first light cable to generate the optical image signal, and the image processing device generates an image capturing the subject under examination by demodulating the optical image signal transmitted by the second light cable.

According to this embodiment, the communication light source is outside the distal unit of the endoscope. It is therefore possible to reduce the impact of heat generation in the distal unit even when a high-output communication light source is used. By using the communication light source that is separate from the illumination light source, optical transmission of a higher quality is realized.

The communication light source may be provided in the image processing device.

The endoscopic system may further comprise a light source controller provided in the image processing device to control an output of the communication light source. The light source controller may control the output of the communication light source based on a light emission intensity of the communication light source.

The light source controller may control the output of the communication light source based on a light intensity of the optical image signal transmitted by the second light cable.

The endoscope may further include a connection unit connectable to the image processing device. The image processing device may further include a photoelectric converter for converting the optical image signal into an electrical image signal, and a fourth light cable for transmitting the optical image signal transmitted by the second light cable to the photoelectric converter. The fourth light cable may have a convex-shaped fiber outgoing end from which the optical image signal outgoes toward the photoelectric converter.

The fourth light cable may be a multimode optical fiber.

A description will be given of the embodiments of the present invention with reference to the drawings. In the explanations of the figures, the same elements shall be denoted by the same reference numerals, and duplicative explanations will be omitted appropriately. The structure described below is by way of example only and does not limit the scope of the present invention.

First Embodiment

FIG. 1 schematically shows a configuration of an endoscopic system 100 according to a first embodiment. The endoscopic system 100 includes an endoscope 10, an image processing device 50, and a display device 60. The endoscope 10 includes an insertion unit 12, a user operation unit 14, and a connection unit 16.

The endoscope 10 is a device configured to capture a video of a target side in a lumen of a subject by inserting the insertion unit 12 in the lumen and orienting a distal unit 18 of the insertion unit 12 toward a subject under observation. The endoscope 10 is a flexible scope in which the insertion unit 12 is made of a flexible material and the orientation of the distal unit 18 is adjustable by bending the neighborhood of the distal unit 18. The distal unit 18 is a portion that accommodates an imaging lens or an imaging device. The outer surface of the distal unit 18 is comprised of a rigid member such as a metal member. For this reason, the distal unit 18 is less flexible than the insertion unit 12.

The user operation unit (also referred to as an endoscope user operation unit) 14 is provided between the insertion unit 12 and the connection unit 16. The user operation unit 14 is a portion held by a user using the endoscope 10 and is provided with a manipulation knob 24 for controlling the orientation of the distal unit 18. The connection unit 16 is provided with a plug 20 for connection with a receptacle 52 of the image processing device 50, and a universal cord 22 connecting the user operation unit 14 and the plug 20. The image signal showing a video captured by the endoscope 10 is transmitted to the image processing device 50 via the plug 20 and processed in the image processing device 50. The image processing device 50 is a so-called video processor that processes the transmitted image signal and displays a video of the subject under observation on the display device 60 such as a liquid crystal display.

Figure 2:
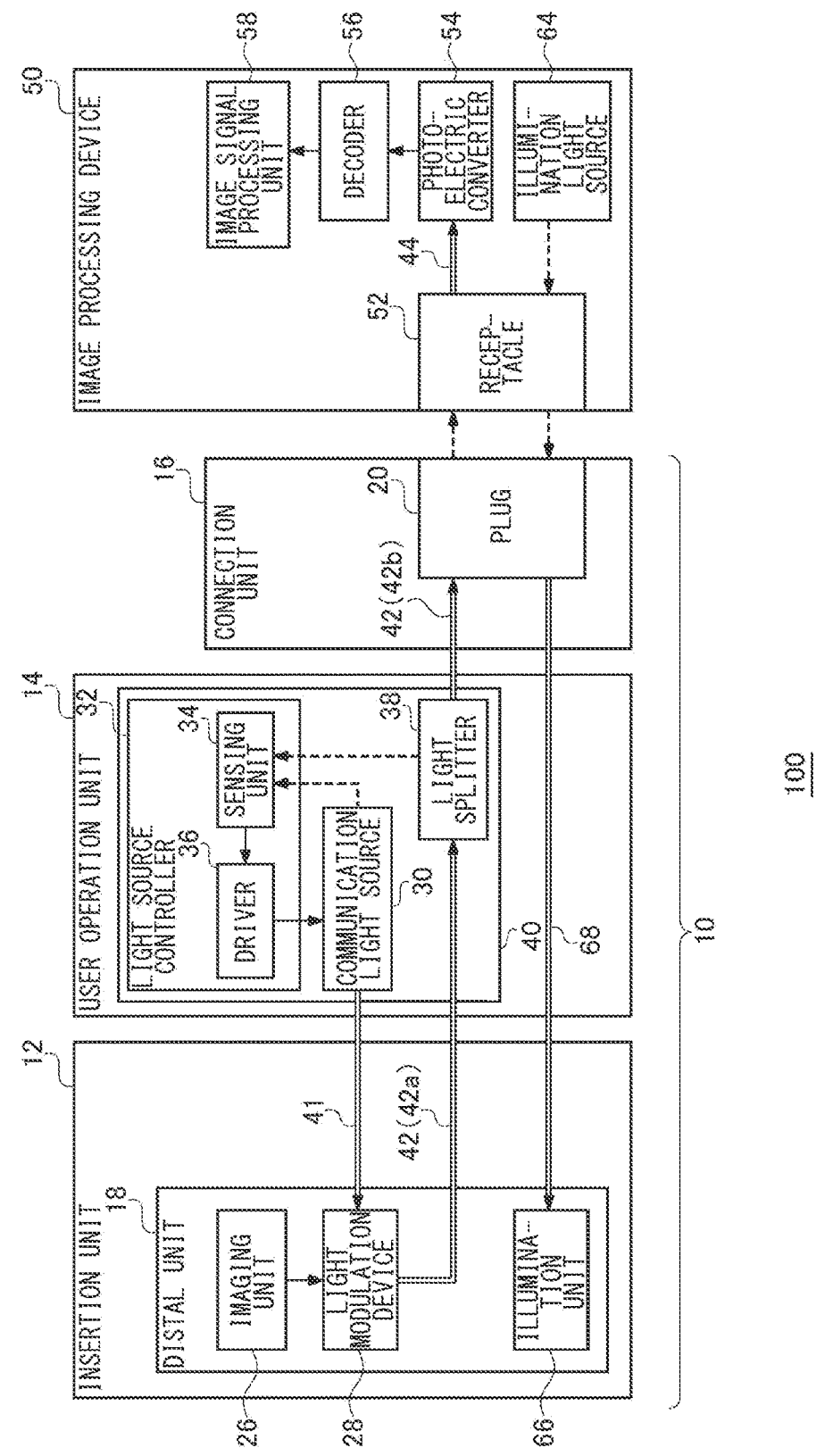
FIG. 2 is a block diagram schematically showing functions and structures of the endoscopic system.

FIG. 2 is a block diagram schematically showing functions and structures of the endoscopic system 100. The endoscope 10 further includes an imaging unit 26, a light modulation device 28, a communication light source 30, a light source controller 32, a light splitter 38, a first light cable 41, a second light cable 42, an illumination unit 66, and an illumination light cable 68.

The imaging unit 26 is provided inside the distal unit 18. The imaging unit 26 includes an imaging optical system including an imaging lens, an imaging device such as a CCD and a CMOS sensor, and a synchronization signal generator for driving the imaging device. The imaging unit 26 captures an image of the subject under observation and outputs an electrical image signal corresponding to the captured image to the light modulation device 28. The imaging unit 26 includes an A/D converter for digitizing the analog electrical image signal and is configured to output a digital electrical image signal to the light modulation device 28. For example, the imaging unit 26 is configured to capture a full-HD video having 1920×108 pixels or videos of larger pixel counts such as 4K and 8K.

The light modulation device 28 is provided in the distal unit 18. The light modulation device 28 outputs an optical image signal based on the electrical image signal output from the imaging unit 26. The light modulation device 28 generates the optical image signal corresponding to the electrical image signal by subjecting light transmitted from the communication light source 30 via the first light cable 41 to intensity modulation. The light modulation device 28 outputs the generated optical image signal to the second light cable 42 (42a).

The communication light source 30 is provided in the user operation unit 14. The communication light source 30 is comprised of a semiconductor light emitting device such as a light emitting diode and a laser diode. The communication light source 30 is a light source different from the illumination light source 64 described later and outputs a single-wavelength light suitable for optical communication. The communication light source 30 is made of, for example, an AlGaAs/GaAs-based material, and a Fabry-Perot laser diode outputting a near infrared wavelength of 800 nm-900 nm may be used. A vertical cavity surface emitting laser (VCSEL) that is a surface-emitting light source may be used as the communication light source 30. The output light from the communication light source 30 is input to the first light cable 41 by using a coupling lens (not shown) such as an aspherical lens.

The light source controller 32 is provided in the user operation unit 14. The light source controller 32 includes a sensing unit 34 for sensing the light intensity, and a driver 36 for operating the communication light source 30 in accordance with the result of sensing by the sensing unit 34. The light source controller 32 drives the communication light source 30 in accordance with the output intensity of the communication light source 30 or the light intensity of the optical image signal transmitted via the second light cable 42 (42a). The light source controller 32 subjects the output of the communication light source 30 to feedback control so that the signal intensity of the optical image signal transmitted by the second light cable 42 is within a predetermined reference range.

The light splitter 38 is a light splitting device for splitting a portion of the optical image signal transmitted by the second light cable 42 and guiding the split signal to the sensing unit 34. The light splitter 38 is a fused fiber coupler produced by heating and fusing two fibers placed in close proximity to each other and then performing fusion splicing and extension. The light splitter 38 is produced by using a section of the second light cable 42. The light splitter 38 transmits the majority of (e.g., 99% or more) of the optical image signal transmitted from the light modulation device 28 toward the plug 20 and causes the small remaining portion (e.g., 1% or less) to branch toward the sensing unit 34.

The first light cable 41 and the second light cable 42 are comprised of a single mode optical fiber and are inserted in the insertion unit 12. The first light cable 41 transmits the output light of the communication light source 30 to the light modulation device 28. The second light cable 42 transmits the optical image signal output from the light modulation device 28 to the plug 20. In the second light cable 42, an upstream section 42a between the light modulation device 28 and the light splitter 38 and a downstream section 42b between the light splitter 38 and the plug 20 are formed by a single optical fiber. The sections 42a and 42b of the second light cable 42 may be formed by separate optical fibers.

The illumination unit 66 is an optical system for illuminating the subject under observation and includes an illumination lens, etc. The illumination light cable 68 is an optical fiber for transmitting the illumination light output from the illumination light source 64 from the plug 20 to the distal unit 18. The illumination light cable 68 is configured as a fiber bundle including a bundle of a plurality of bare optical fibers and is inserted in the insertion unit 12, the user operation unit 14, and the connection unit 16.

The image processing device 50 includes the receptacle 52, a light transmission cable 44, a photoelectric converter 54, a decoder 56, an image signal processing unit 58, and the illumination light source 64.

The receptacle 52 is configured to be connected to the plug 20 and causes the optical image signal transmitted by the second light cable 42 (42b) to be input to the fourth light cable 44. The receptacle 52 also causes the illumination light output from the illumination light source 64 to be input to the illumination light cable 68.

The light transmission cable (also referred to as the fourth light cable) 44 is an optical fiber provided in the image processing device 50 and transmits the optical image signal from the receptacle 52 to the photoelectric converter 54. The light transmission cable 44 is comprised of a multimode fiber. By configuring the light transmission cable 44 as a multimode fiber, it is possible restrict reduction in the efficiency of coupling between the second light cable 42 (42b) and the light transmission cable 44 even if a slight misalignment occurs as the plug 20 and the receptacle 52 are coupled. In one variation, the light transmission cable 44 may be configured as a single mode fiber. Alternatively, both the second light cable 42 and the light transmission cable 44 may be configured as a multimode optical fiber. In that case, the requirement for positioning accuracy at a joint between the light modulation device 28 and the second light cable 42 is moderated.

The photoelectric converter 54 converts the optical image signal transmitted from the endoscope 10 into an electrical image signal. For example, the photoelectric converter 54 may include a light receiving sensor such as a photo diode, a transimpedance amplifier (TIA) for converting a current value output from the light receiving sensor into a voltage value, and a limiting amplifier (RMA) for amplifying the output from the TIA. The light receiving sensor may be made of an InGaAs-based or Si-based material having a high light receiving sensitivity in the near infrared range. The decoder 56 demodulates the electric image signal from the photoelectric converter 54 into a video signal. The image signal processing unit 58 processes the demodulated video signal and displays the processed signal on the display device 60 such as a liquid crystal display.

The illumination light source 64 outputs illumination light for illuminating the subject under observation. The illumination light source 64 is comprised of, for example, a xenon lamp that emits white light similar to natural light. The illumination light source 64 may be configured to output light of a limited wavelength band in order to realize narrow band optical observation. Still alternatively, the illumination light source 64 may be configured as a light source device independent from the image processing device 50 instead of being provided in the image processing device 50.

Figure 3:
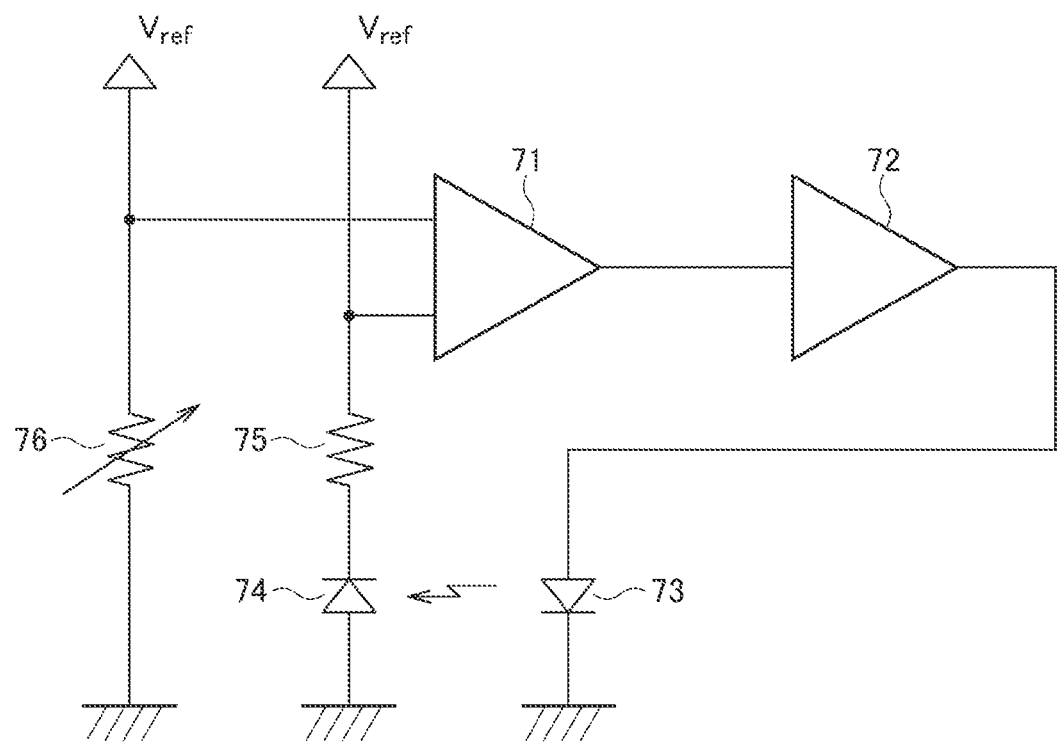
FIG. 3 is a circuit diagram schematically showing an exemplary configuration of the light source controller.

FIG. 3 is a circuit diagram schematically showing an exemplary configuration of the light source controller 32. A circuit 70 includes a comparator 71 comprised of an operational amplifier or the like, a driver 72 comprised of a transistor or the like, a laser diode 73, a photo diode 74, a current sensing resistor 75, and a variable resistor 76. Comparing the configuration of FIG. 3 with the configuration of FIG. 2, the comparator 71 and the driver 72 correspond to the driver 36, the laser diode 73 corresponds to the communication light source 30, and the photo diode 74 corresponds to the sensing unit 34.

The circuit 70 senses the output intensity of the laser diode 73 in the photo diode 74 and the current sensing resistor 75 and compares, in the comparator 71, the sensed voltage value with a target voltage value configured as desired by using the variable resistor 76. The comparator 71 controls the output of the driver 72 in accordance with the difference between these voltage values and subjects the output of the laser diode 73 to feedback control. The circuit 70 mainly adjusts variation of about several Hz-several hundred Hz, which is sufficiently smaller than the signal frequency of the optical image signal subjected to intensity modulation by the light modulation device 28. The variation is caused by a change in the operating environment such as temperature or a time-dependent change in components forming the endoscope 10. Therefore, the circuit 70 may be formed by relatively inexpensive components having operating frequencies that are not so high.

The circuit 70 may be formed by mounting the components on a printed substrate or a flexible substrate. Alternatively, the circuit 70 may be built by forming the components on the same substrate such as a silicon substrate and a quartz substrate by using a semiconductor process. In the latter case, the light splitter 38 may be formed on the substrate on which the circuit 70 is formed in an integrated manner, by manufacturing the light splitter 38 using a technique for plane type light waveguides. By forming the communication light source 30, the light source controller 32, and the light splitter 38, which are provided in the user operation unit 14, on a same substrate 40 for size reduction (see FIG. 2), the limited space in the user operation unit 14 is effectively utilized.

Figure 4:
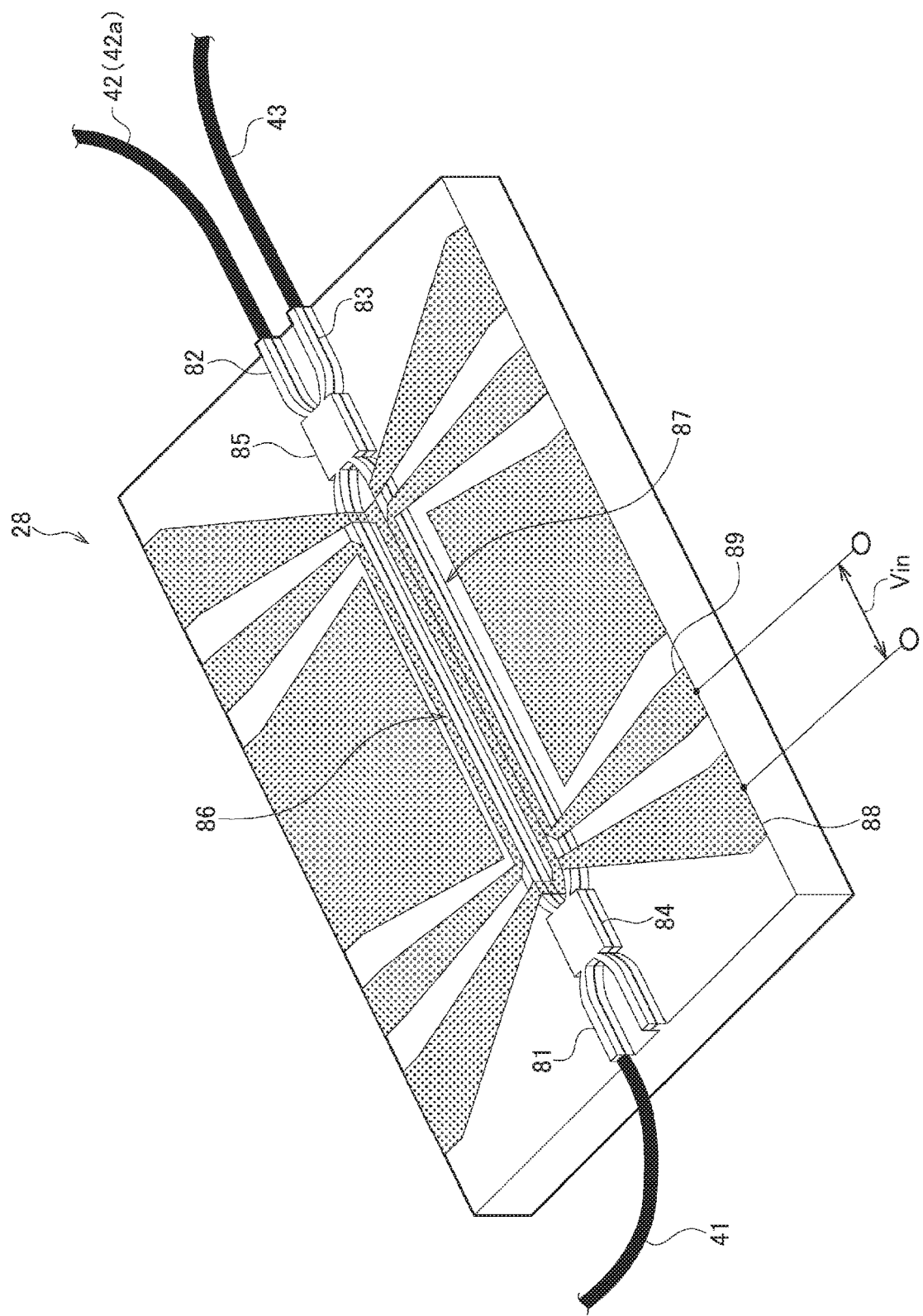
FIG. 4 is a perspective view schematically showing an exemplary configuration of the light modulation device.

FIG. 4 is a perspective view schematically showing an exemplary configuration of the light modulation device 28. The illustrated light modulation device 28 is a Mach-Zehnder light intensity modulator manufactured by using a technique for plane type light waveguides and uses interference of light propagating on two light paths to demodulate the light intensity. The light modulation device 28 includes an input port 81, a first output port 82, a second output port 83, an input side coupler 84, an output side coupler 85, a first light waveguide 86, a second light waveguide 87, a first electrode 88, and a second electrode 89.

The first light cable 41 is connected to the input port 81, and the second light cable 42 (42*a*) is connected to the first output port 82. A third light cable 43 (used in the second embodiment described later) can be connected to the second output port 83. Each light cable can be connected by directly connecting the fiber end face to the respective port by fusion splicing. The input side coupler 84 and the output side coupler 85 are multi-mode interference coupler (MMI) that uses multi-mode interference.

The light input to the input port 81 is branched in the input side coupler 84 and is guided through the first light waveguide 86 and the second light waveguide 87. The first light waveguide 86 and the second light waveguide 87 are made of a material having an electrooptic effect such that the light path lengths from the input side coupler 84 to the output side coupler 85 are identical. The second light waveguide 87 is configured such that the refractive index of the waveguide varies depending on a voltage Vin applied across the first electrode 88 and the second electrode 89. As a result, a phase difference is created between the light guided by the waveguides 86 and 87 depending on the applied voltage Vin.

The light guided by the waveguides 86 and 87 is combined by the output side coupler 85 and output from the first output port 82 and the second output port 83. When the phases of the light guided by the waveguides 86 and 87 match, the interference in the output side coupler 85 causes the light to be output from the first output port 82 but does not cause the light to be output from the second output port 83. Meanwhile, when the phases of the light guided by the waveguides 86 and 87 are inverted, the interference causes the light not to be output from the first output port 82 and causes the light to be output from the second output port 83. Thus, the light modulation device 28 modulates the intensity of the light output from the first output port 82 and the second output port 83 in accordance with the applied voltage Vin.

Figure 5A:
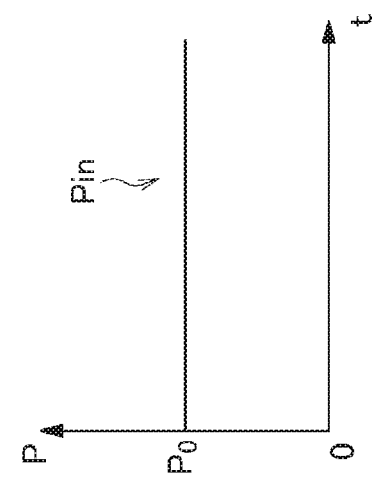
FIGS. 5A-5C are graphs schematically showing the input and output signals of the light modulation device.
Figure 5B:
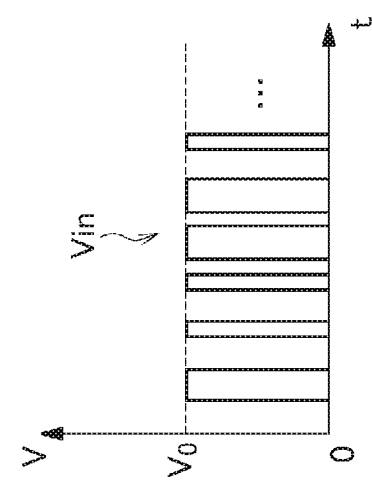
Figure 5C:
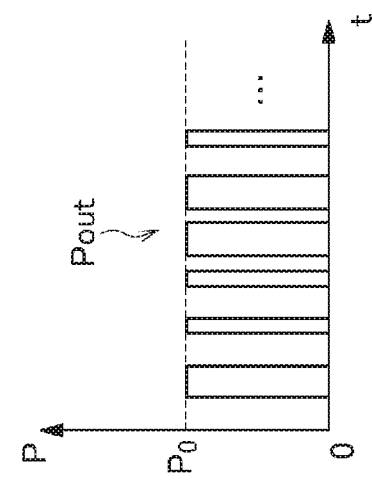

FIGS. 5A-5C are graphs schematically showing the input and output signals of the light modulation device 28. FIG. 5A shows an intensity waveform Pin of the light input to the input port 81. The light input to the input port 81 is the output light of the communication light source 30 for which the light amount is not modulated and is a continuous light (CW) having a constant intensity value of P0. FIG. 5 shows the voltage waveform Vin applied across the electrodes of the light modulation device 28. The voltage waveform Vin is the digital electrical image signal output from the imaging unit 26. FIG. 5C shows an intensity waveform Pout of the light output from the first output port 82. As shown in the figure, the output light from the first output port 82 is modulated into a pulsed optical image signal in accordance with the voltage waveform Vin. In this way, the light modulation device 28 generates an optical image signal and outputs the generated optical image signal to the second light cable 42.

Figure 6:
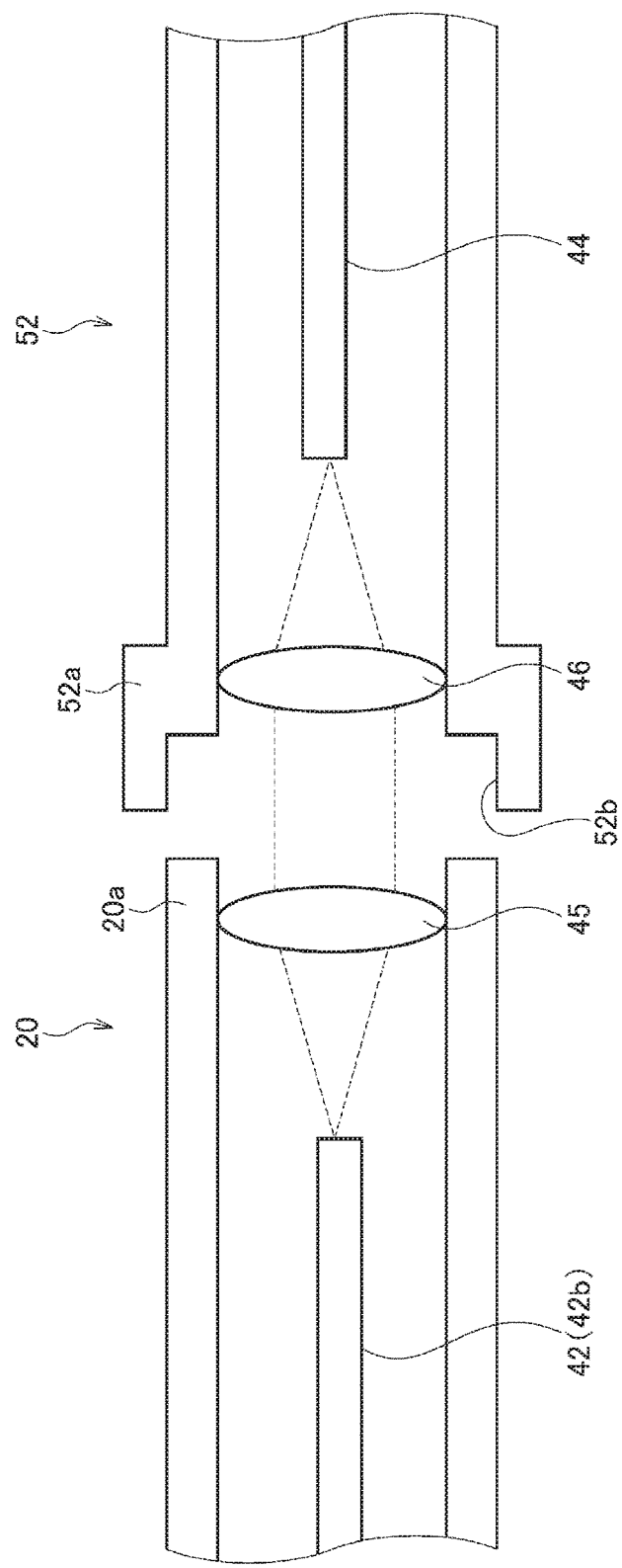
FIG. 6 schematically shows a structure of the plug and the receptacle.

FIG. 6 schematically shows a structure of the plug 20 and the receptacle 52 and shows a coupling structure for the second light cable 42 (42*b*) and the light transmission cable 44. The receptacle 52 has a recess 52*b* engageable with a connection end 20*a* of the plug 20. The receptacle 52 is configured such that the second light cable 42 and the light transmission cable 44 are optically coupled by engaging the connection end 20*a* and the recess 52*b*. In other words, the plug 20 and the receptacle 52 are positioned such that the light axes of the second light cable 42 and the light transmission cable 44 are aligned when the plug 20 and the receptacle 52 are coupled.

A coupling lens 45 formed by an aspheric lens or the like is provided at the connection end 20*a* of the plug 20. The coupling lens 45 transforms the diverging light output from the outgoing end of the second light cable 42 into parallel light. Similarly, a coupling lens 46 formed by an aspheric lens or the like is provided at a connection end 52*a* of the receptacle 52. The coupling lens 46 condenses the parallel light outgoing from the connection end 20*a* and couples the condensed light to the light transmission cable 44.

Figure 7A:
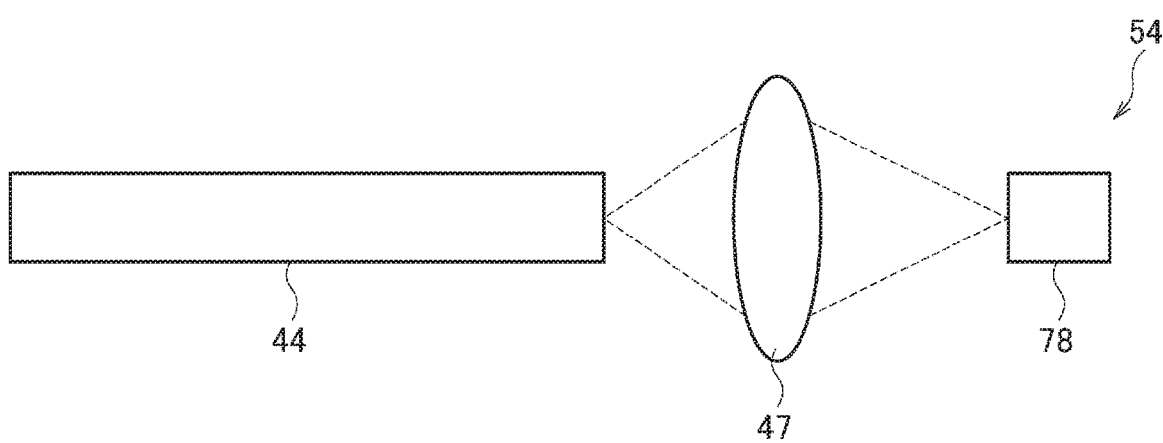
FIGS. 7A and 7B schematically show a coupling structure for the fourth light cable and the photoelectric converter.
Figure 7B:
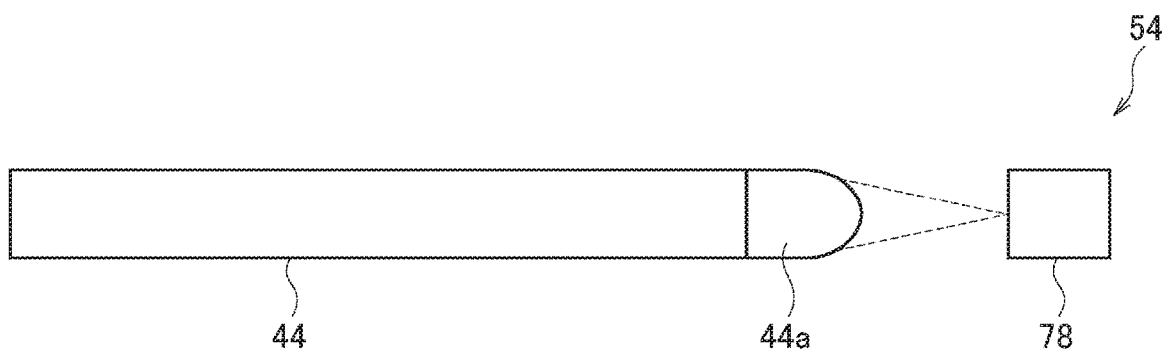

FIGS. 7A and 7B schematically show a coupling structure for the light transmission cable 44 and the photoelectric converter 54. FIG. 7A shows a case of using a coupling lens 47. As illustrated, the optical image signal outgoing from the light transmission cable 44 is condensed by the coupling lens 47 on a light receiving sensor 78 of the photoelectric converter 54.

FIG. 7B shows a case of using a lensed fiber in which the outgoing end 44*a* of the light transmission cable 44 is worked into a convex shape. In this case, the optical image signal outgoing from the light transmission cable 44 is condensed by the outgoing end 44*a* in the convex shape on the light receiving sensor 78. The lensed fiber like this can be realized by fitting a microlens on the fiber end face by adhesion or fusion splicing or by working the fiber end face into a lens shape by polishing or discharging.

A description will now be given of the operation of the endoscopic system 100 having the above configuration. The insertion unit 12 is inserted into the lumen of the subject and the distal unit 18 is oriented toward the subject under observation. The imaging unit 26 captures an image of the subject under observation illuminated by the illumination unit 66 and outputs an optical image signal to the light modulation device 28. The communication light source 30 is driven so that the output intensity of the communication light source 30 or the intensity of the optical image signal is within a predetermined reference range and outputs continuous light to the light modulation device 28 via the first light cable 41. The light modulation device 28 modulates the continuous light from the communication light source 30 based on the electrical image signal and outputs the optical image signal to the image processing device 50 via the second light cable 42. The image processing device 50 generates a video signal by modulating the optical image signal received via the light transmission cable 44 and causes the display device 60 to display a video of the subject under observation.

According to the embodiment, instead of providing the communication light source 30 in the distal unit 18 characterized by severe spatial constraint and thermal constraint, the communication light source 30 is provided in the user operation unit 14 characterized by relatively less severe constraints. Therefore, the high-output communication light source 30 can be used. As a result, the optical image signal with more excellent signal to noise ratio (S/N ratio) can be transmitted to the image processing device 50 as compared with the case of providing the light source in the distal unit 18. Further, since the communication light source 30 as a source of heat is not provided in the distal unit 18, the thermal constraint on the imaging unit 26 and the light modulation device 28 can be restricted. As a result, the imaging unit 26 and the light modulation device 28 can be operated at a higher speed, and an image signal of a higher definition and larger amount of information can be transmitted. Thus, according to this embodiment, the impact of heat in the distal unit 18 is reduced and the image quality of the endoscopic system 100 is enhanced.

In accordance with this embodiment, the communication light source 30 is subject to feedback control by using the light intensity of the optical image signal modulated by the light modulation device 28 and transmitted by the second light cable 42. Therefore, the intensity of the optical image signal transmitted to the image processing device 50 is maintained within a predetermined reference range. While the endoscope 10 is being in use, the insertion unit 12 is in a bent state so that the first light cable 41 and the second light cable 42 inserted therein are also in a bent state. As a result, the transmission efficiency in the first light cable 41 and the second light cable 42 may be lowered and the intensity of the optical image signal arriving at the image processing device 50 may be lowered. In this embodiment, the light intensity of the optical image signal is sensed at the position of the user operation unit 14 so that, even when the signal intensity is lowered due to the bending of the insertion unit 12, the output of the communication light source 30 can be subjected to feedback control to compensate for the amount in which the signal intensity is lowered. Further, by controlling the intensity of the optical image signal output from the plug 20 not to be too high, output of a high-intensity laser beam from the plug 20 is prevented from occurring when the plug 20 is removed from the receptacle 52. Thus, according to this embodiment, the reliability of the endoscopic system 100 is enhanced.

In accordance with the embodiment, the communication light source 30 can be provided at a position distanced from the imaging device that generates a relatively large amount of heat, the device life is prevented from being reduced due to the operation of the communication light source 30 in a high temperature.

In accordance with the embodiment, the first light cable 41 and the second light cable 42 inserted in the insertion unit 12 are configured as a single mode fiber having a small diameter. Therefore, the impact of an increase in the diameter of the insertion unit 12 due to the addition of the light cable is reduced. Further, the light transmission cable 44 provided in the image processing device 50 is configured as a multimode fiber so that the impact of coupling loss on the receiving side of the optical image signal is reduced.

In accordance with the embodiment, the high-intensity optical image signal can be transmitted to the image processing device 50 so that the requirement for the positioning accuracy the optical path in the image processing device 50 is moderated. More specifically, the signal intensity sufficient for demodulation of the video signal can be secured in the presence of a large coupling loss in the coupling structure for the plug 20 and the receptacle 52 or the coupling structure for the light transmission cable 44 and the photoelectric converter 54 resulting from moderating the requirement for positioning accuracy of the components. Accordingly, the embodiment reduces the cost to build the endoscopic system 100 or the cost incurred by using components with high positioning accuracy.

Second Embodiment

Figure 8:
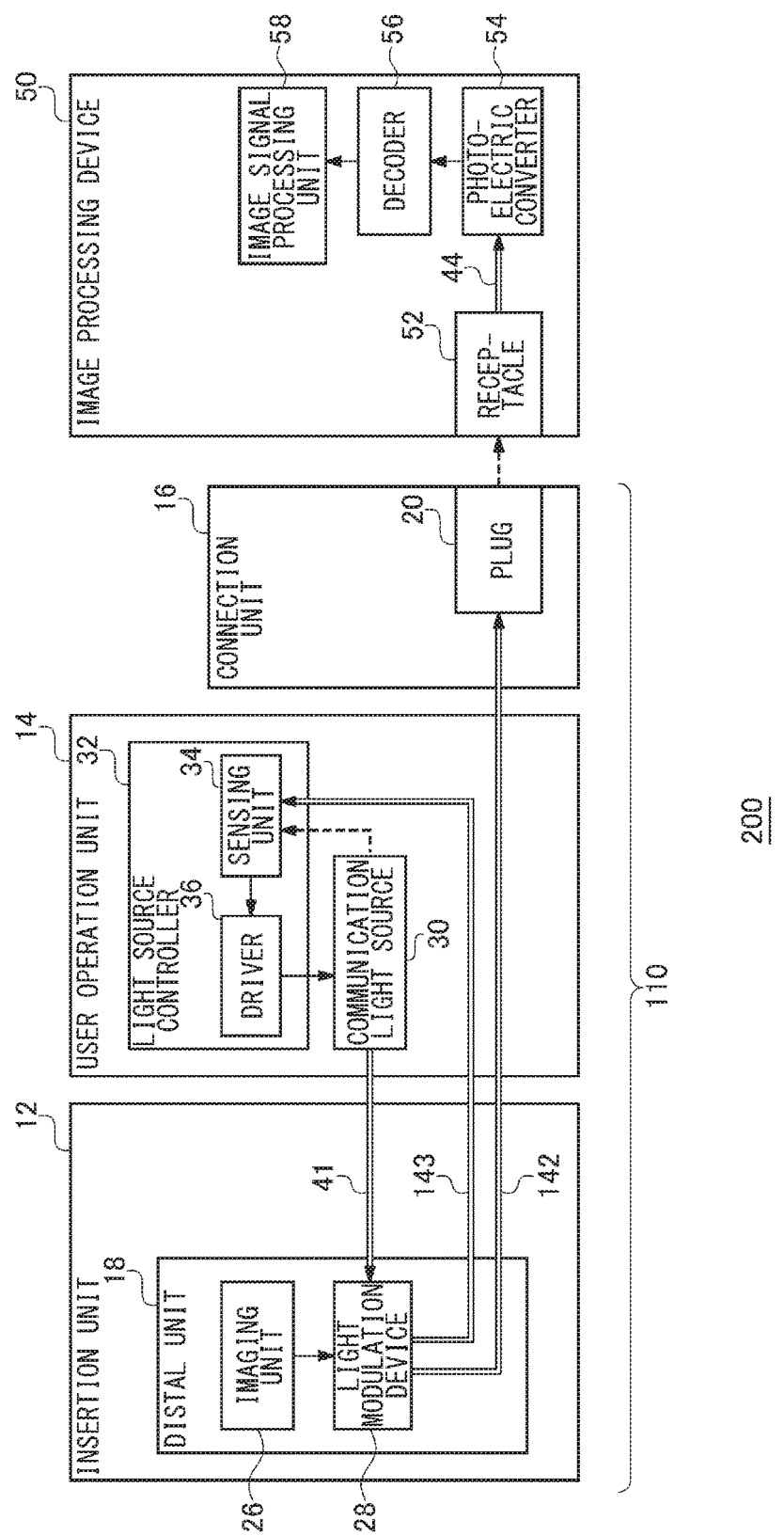
FIG. 8 is a block diagram schematically showing a configuration of an endoscopic system according to an embodiment.

FIG. 8 is a block diagram schematically showing a configuration of an endoscopic system 200 according to the second embodiment. The endoscopic system 200 differs from the first embodiment in that a second light cable 142 and a third light cable 143 are connected to the output of the light modulation device 28. A description will be given of the endoscopic system 200, highlighting differences from the first embodiment.

The endoscopic system 200 includes an endoscope 110 and an image processing device 50. The endoscope 110 includes the insertion unit 12, the user operation unit 14, the connection unit 16, the distal unit 18, the plug 20, the imaging unit 26, the light modulation device 28, the communication light source 30, the light source controller 32, the first light cable 41, a second light cable 142, and a third light cable 143. The light source controller 32 includes the sensing unit 34 and the driver 36. In FIG. 8, the components for illuminating the subject under examination (e.g., the illumination light source 64, the illumination unit 66, the illumination light cable 68) are omitted.

The second light cable 142 is provided between the light modulation device 28 and the plug 20 and transmits the optical image signal output from the light modulation device 28 to the plug 20. The second light cable 142 corresponds to the second light cable 42 of FIG. 4 and is connected to the first output port 82 of the light modulation device 28.

The third light cable 143 is provided between the light modulation device 28 and the sensing unit 34 and transmits the optical image signal output from the light modulation device 28 to the sensing unit 34. The third light cable 143 corresponds to the third light cable 43 of FIG. 4 and is connected to the second output port 83 of the light modulation device 28. For example, the third light cable 143 transmits an optical image signal derived from inverting the phase of the optical image signal transmitted by the second light cable 142.

According to this embodiment, by connecting the two light cables 142 and 143 to the light modulation device 28, the optical image signal can be transmitted to both the plug 20 and the sensing unit 34 without using the light splitter 38 according to the first embodiment. As a result, the transmission loss of the optical image signal produced in the light splitter 38 is eliminated and the signal intensity of the optical image signal transmitted to the image processing device 50 is increased. Thus, according to this embodiment, the S/N of the optically transmitted signal is improved and, further, the cost is reduced by eliminating the need for the light splitter.

Third Embodiment

Figure 9:
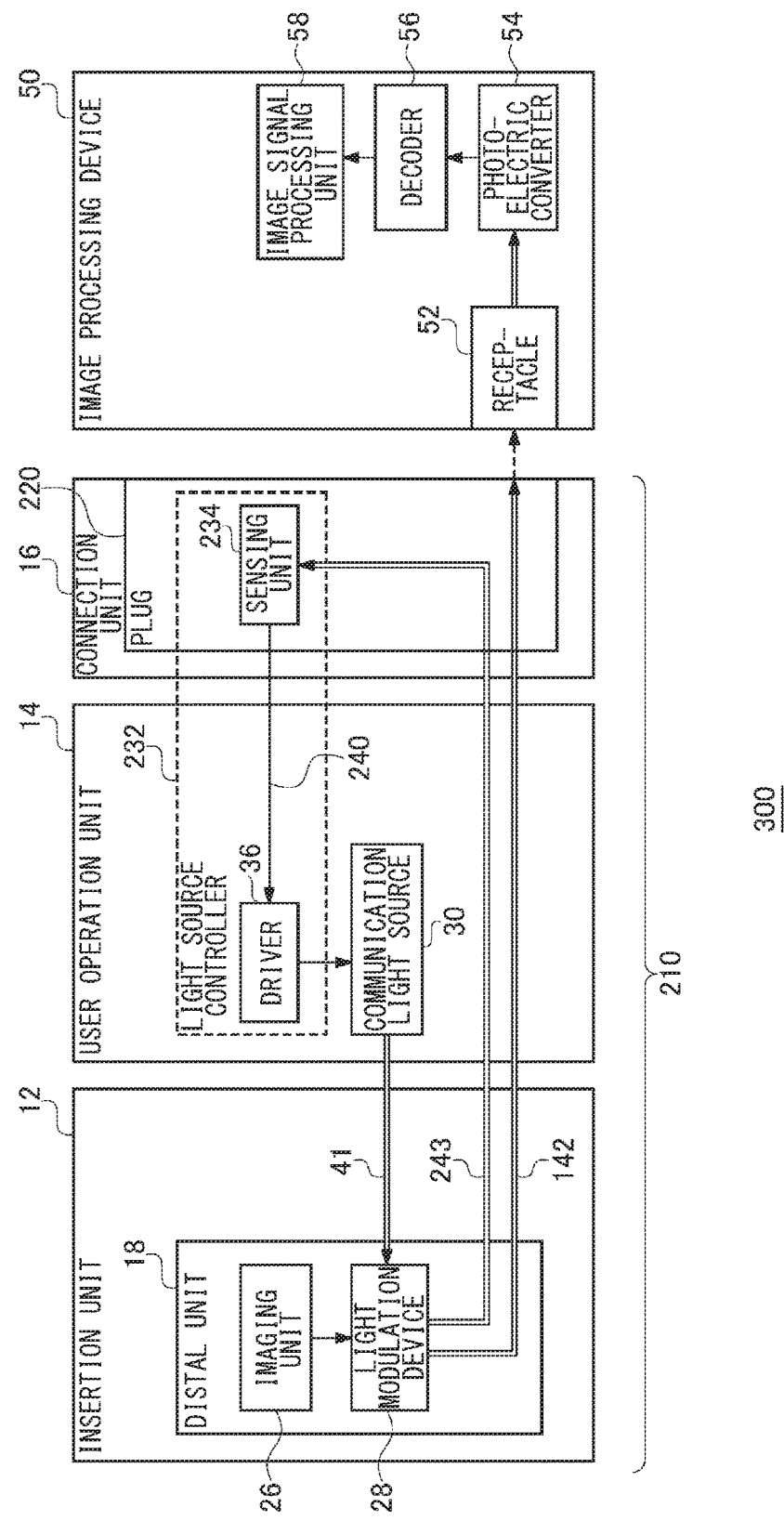
FIG. 9 is a block diagram schematically showing a configuration of an endoscopic system according to an embodiment.

FIG. 9 is a block diagram schematically showing a configuration of an endoscopic system 300 according to the third embodiment. The endoscopic system 300 differs from the second embodiment in that a sensing unit 234 for sensing the intensity of the optical image signal is provided in a plug 220 of the connection unit 16 instead of in the user operation unit 14. A description will be given of the endoscopic system 300, highlighting differences from the second embodiment.

The endoscopic system 300 includes an endoscope 210 and the image processing device 50. The endoscope 210 includes the insertion unit 12, the user operation unit 14, the connection unit 16, the distal unit 18, a plug 220, the imaging unit 26, the light modulation device 28, the communication light source 30, a light source controller 232, a first light cable 141, the second light cable 142, and a third light cable 243. The light source controller 232 includes a sensing unit 234 and the driver 36.

The sensing unit 234 is provided in the plug 220 of the connection unit 16 and senses the optical image signal transmitted by the third light cable 243. The third light cable 243 is provided between the light modulation device 28 and the sensing unit 234 and transmits the optical image signal output from the light modulation device 28 to the sensing unit 234. The sensing unit 234 transmits the detected value of the optical image signal to the driver 36 as an electrical signal via a signal line 240. The driver 36 is provided in the user operation unit 14 and drives the communication light source 30 based on the electrical signal from the sensing unit 234.

According to this embodiment, an extra space is created inside the user operation unit 14 by providing the sensing unit 234 in the plug 220. In order to sense the optical image signal from the third light cable 243 efficiently by using the sensing unit 234, a coupling structure such as a coupling lens may be required. Due to the space constraint inside the user operation unit 14, it may be difficult to include the sensing unit 234 and the coupling structure for coupling to the sensing unit 234, in addition to the communication light source 30 and the driver 36. According to the embodiment the space constraint is moderated, and the design flexibility is improved by dividing the constituting elements of the light source controller 232 into those for mounting in the user operation unit 14 and those for mounting in the connection unit 16.

In one variation, a light splitter for branching the second light cable 142 may be provided in the plug 220 instead of providing the third light cable 243. In this case, a portion of the optical image signal transmitted by the second light cable 142 is split to branch in the light splitter inside the plug 220 and is transmitted to the sensing unit 234 in the plug 220.

In a further variation, the light source controller 232 including the sensing unit 234 and the driver 36 may be provided in the connection unit 16, the communication light source 30 may be provided in the user operation unit 14, and the drive signal from the driver 36 to the communication light source 30 may be transmitted from the connection unit 16 to the user operation unit 14 as an electrical signal. Still alternatively, both the light source controller 232 and the communication light source 30 may be provided in the connection unit 16, and the first light cable 41, the second light cable 142, and the third light cable 243 may be provided between the connection unit 16 and the insertion unit 12. In other words, an arbitrary portion of the set of the communication light source 30 and the light source controller 232 may be provided in the connection unit 16 or the entirety thereof may be provided in the connection unit 16. According to this variation, the units can be arranged and connected to adapt to the permitted space in the user operation unit 14 and the connection unit 16 so that the design flexibility is improved.

Described above is an explanation based on an exemplary embodiment. The embodiment is intended to be illustrative only and it will be understood by those skilled in the art that various modifications to constituting elements and processes could be developed and that such modifications are also within the scope of the present invention.

Figure 10:
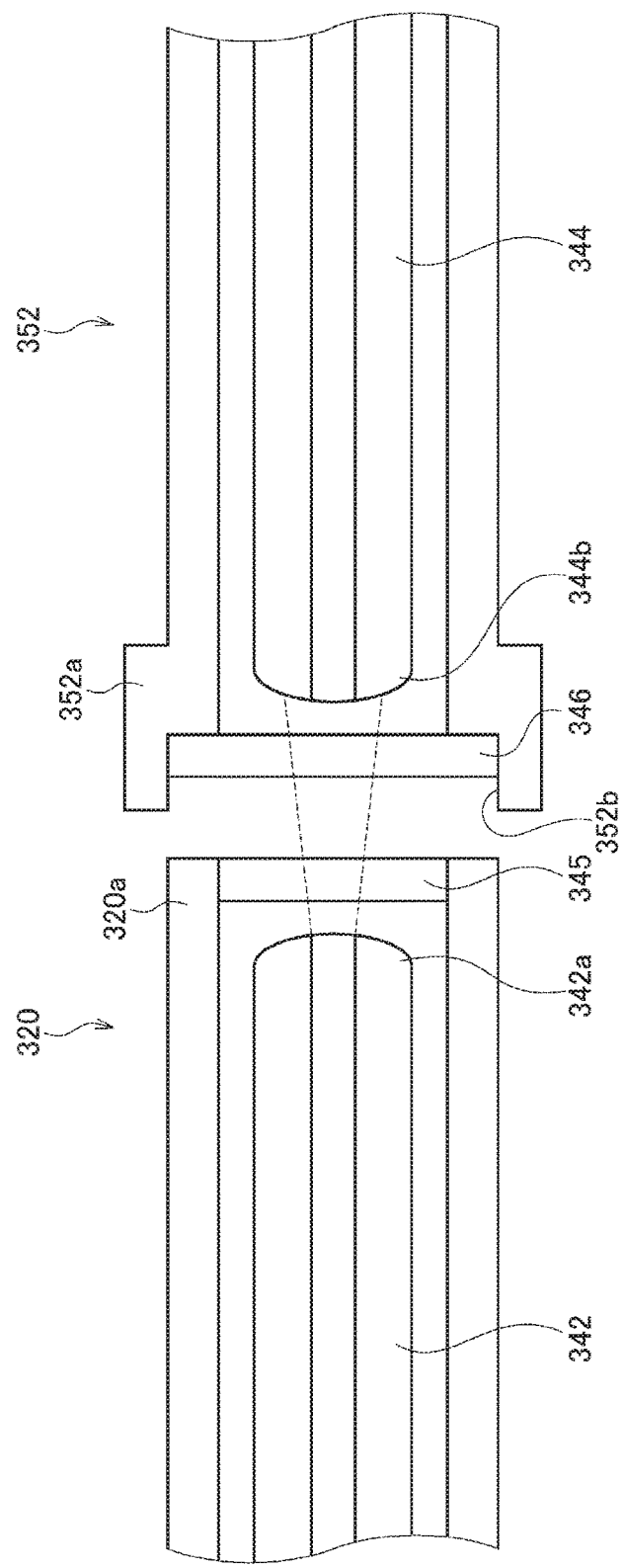
FIG. 10 schematically shows a structure of the plug and the receptacle according to a variation.

FIG. 10 schematically shows a configuration of a plug 320 and a receptacle 352 according to a variation. In the embodiments described above, the coupling lenses 45 and 46 are described as being used as a coupling structure shown in FIG. 6 for the plug 20 and the receptacle 52. In this variation, an outgoing end 342a of a second light cable 342 and an incidence end 344b of a light transmission cable 344 are turned into a convex shape to provide a coupling structure.

As shown in the figure, a cover glass 345 for protecting the outgoing end 342a is provided at a connection end 320a of the plug 320 and a cover glass 346 for protecting the incidence end 344b is provided at a connection end 352a of the receptacle 352. The plug 320 is engaged with a recess 352b of the receptacle 352 and couples the optical image signal output from the second light cable 342 to the light transmission cable 344. As mentioned above, the optical image signal transmitted by the second light cable 342 is of a high intensity so that the optical image signal sufficient for demodulation of a video signal can be transmitted to the image processing device 50 by using the coupling structure according to this variation.

In the coupling structure for the plug 320 and the receptacle 352, the end face of only one of the light cables may be turned into a convex shape and a coupling lens may be provided at the end face of the other light cable.

Figure 11:
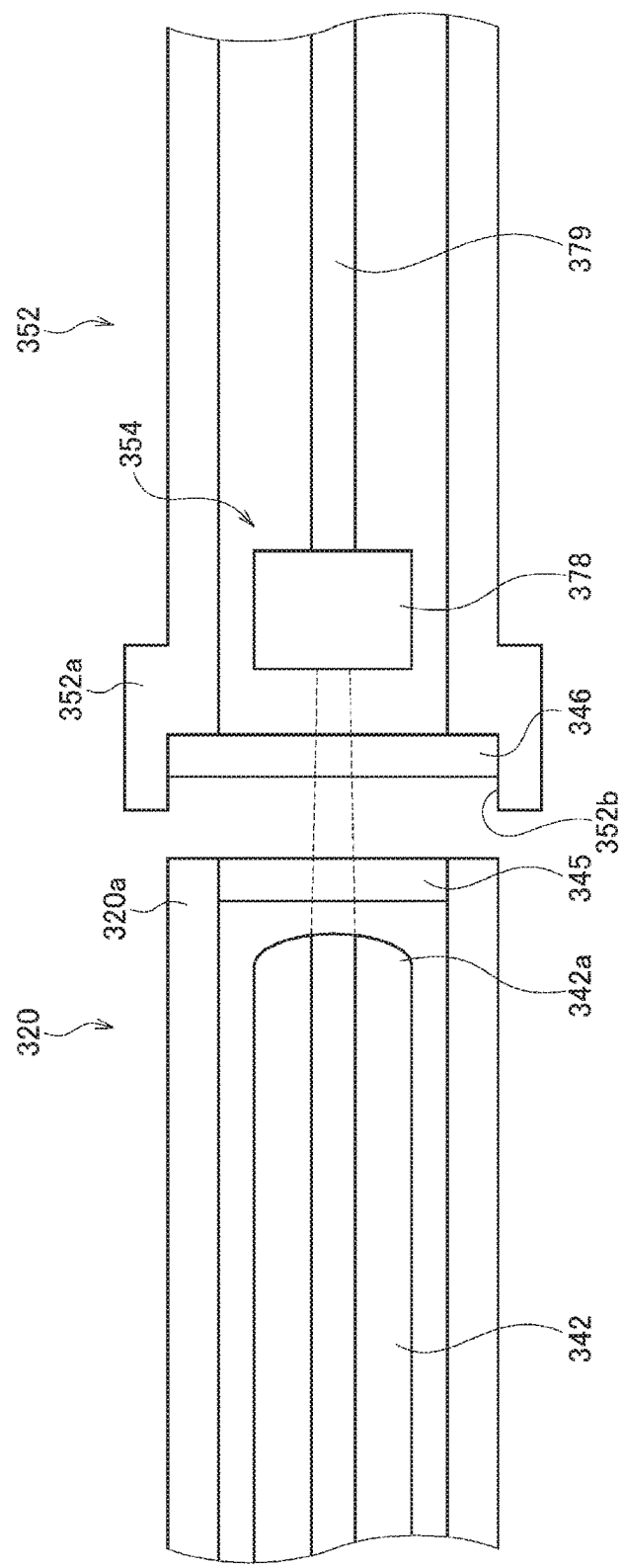
FIG. 11 schematically shows a structure of the plug and the receptacle according a variation.

FIG. 11 schematically shows a structure of the plug 320 and the receptacle 352 according another variation. In this variation, a light receiving sensor 378 forming a photoelectric converter 354 is provided in the receptacle 352 instead of providing the light transmission cable 344. The light receiving sensor 378 is provided in the vicinity of the connection end 352a of the receptacle 352 and is configured to receive the optical image signal condensed by the outgoing end 342a of the second light cable 342. The light receiving sensor 378 is connected an electrical cable 379 provided in the receptacle 352 and outputs an electrical image signal to the transimpedance amplifier (TIA) and the limiting amplifier (RMA) forming the photoelectric converter 354 via the electrical cable 379. According to this variation, the coupling structure for the light transmission cable 44 and the light receiving sensor 78 as shown in FIGS. 7A and 7B is eliminated so that the transmission efficiency is improved and the cost for components is reduced.

In a further alternative, the light receiving sensor, the transimpedance amplifier, the limiting amplifier, etc. forming the photoelectric converter 354 may all be provided in the receptacle 352. In this case, the electrical image signal output from the photoelectric converter 354 provided in the receptacle 352 may be transmitted to the decoder 56 via an electrical cable.

In the third embodiment described above, the sensing unit 234 is described as being provided in the plug 220. In a further variation, both the communication light source and the driver may be provided in the plug 220. In this case, the first light cable may be provided to extend from the plug 220 in the user operation unit 14 to the light modulation device 28 in the distal unit 18.

In the embodiments described above, an AlGaAs/GaAs-based semiconductor light emitting device capable of outputting a single-wavelength light of a wavelength band of 800 nm-900 nm is described as being used in the communication light source. In a variation, a GaInAsP/InP-based semiconductor light emitting device of a wavelength band of 1200 nm-1400 nm may be used. In this case, it is desirable to use a light receiving device made of an InGaAs-based material as the light receiving sensor. By selecting the wavelength band such as this, it is possible to use an optical image signal of an even higher intensity within the range permitted in Standard for Safe Use of Lasers.

Figure 12:
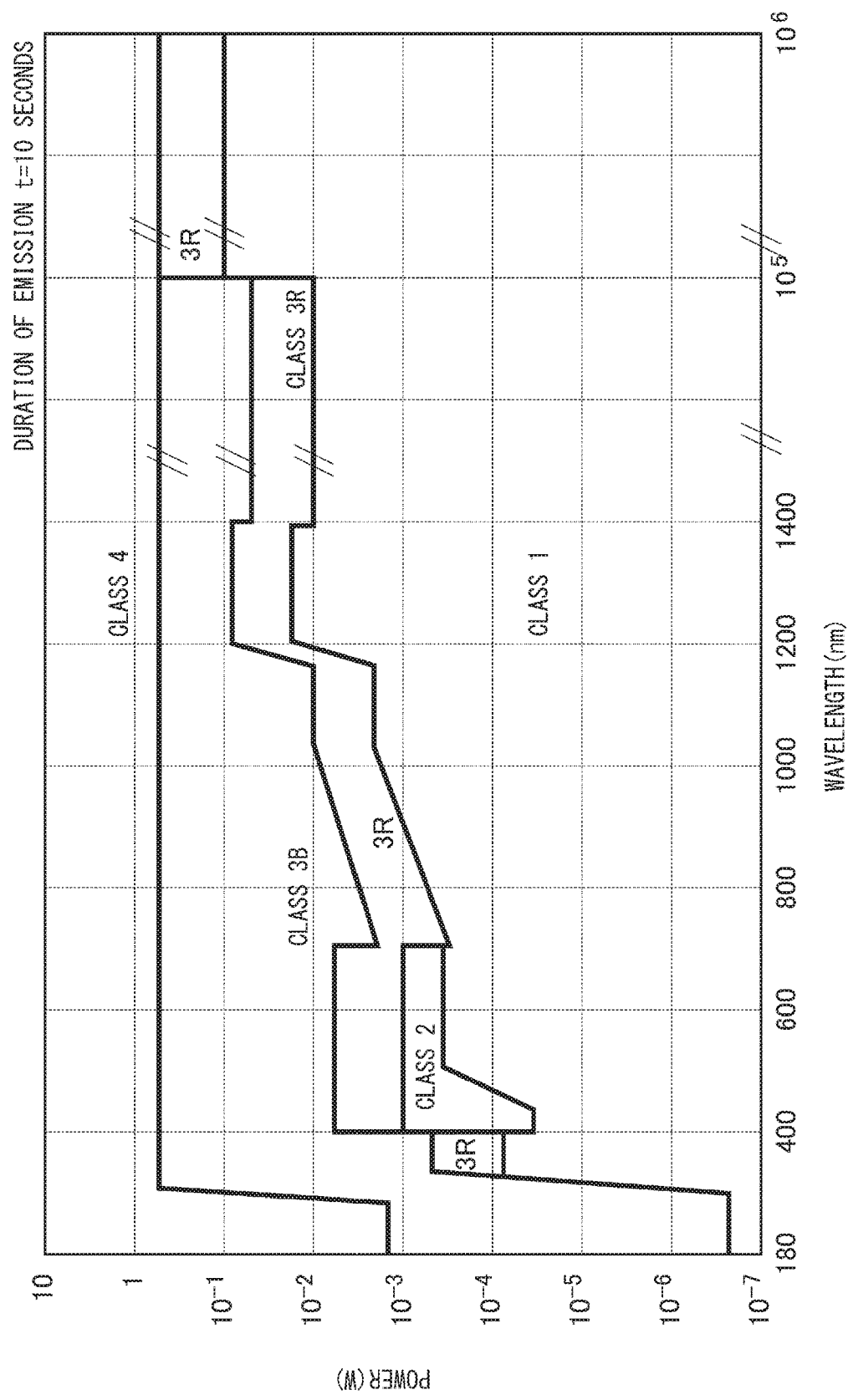
FIG. 12 is a graph showing classification defined in Standard for Safe Use of Lasers.

FIG. 12 is a graph showing classification defined in Standard for Safe Use of Lasers. As illustrated, the upper limit intensity classified as Class 1 is higher in the wavelength band of 1200 nm-1400 nm than in the wavelength bands above and below. The light intensity in excess of 10 mW can be used within the range of Class 1. Therefore, by using a laser light source of a wavelength band of 1200 nm-1400 nm as a communication light source, it is possible to improve the transmission quality by using an optical image signal of an even higher intensity while also meeting the safety requirement at the same time.

In a further variation, the communication light source may output a plurality of single-wavelength light beams, the light modulation device may modulate the plurality of single-wavelength light beams to output a plurality of optical image signals, and the image processing device 50 may receive the plurality of optical image signals. In this case, the communication light source may be formed by a plurality of semiconductor light emitting devices of different output wavelengths and a plurality of different light modulation devices may be used depending on the wavelength. Still alternatively, a light splitter provided in the light modulation device or at the input port of the light modulation device may split the light from the communication light source outputting a single-wavelength light so as to output a plurality of optical image signals. A multicore fiber may be used as a transmission channel from the communication light source to the light modulation device or a transmission channel from the light modulation device to the image processing device. Still alternatively, wavelength division multiplexing may be used to cause one single mode fiber to transmit a plurality of optical image signals of different wavelengths. When a multicore fiber is used, the wavelengths of the respective transmission channels may be identical. A VCSEL array may be used as the communication light source.

In a further variation, the control signal transmitted from the image processing device 50 the imaging unit 26 may be optically transmitted by using a light cable. For example, a light cable different from the first light cable and the second light cable may be inserted in the endoscope 10 to optically transmit a clock signal or a control signal supplied to the imaging device or the driver circuit for the imaging device.

In a further variation, the light source controller may be provided in the image processing device 50. In this case, the communication light source may be provided in the image processing device 50 and continuous light for optical communication may be supplied from the image processing device 50 to the light modulation device 28. Further, the communication light source may be provided in the user operation unit 14 or the connection unit 16 and the drive signal may be output from the image processing device 50 to the communication light source.

In a further variation, the illumination light source may be provided in the endoscopic device instead of the image processing device 50. The illumination light source may be provided in the user operation unit 14 or the connection unit 16, or in the distal unit 18. Where the illumination light source is provided in the distal unit 18, a light emitting diode capable of outputting white light may be used.

The endoscopic device according to the embodiments is described as being a flexible scope. In a variation, the endoscopic device may be a rigid scope configured such that the insertion unit is not flexible. The endoscopic device may find medical applications or industrial applications.

What is claimed is:

1. An endoscope comprising:
   an insertion unit including a distal unit oriented toward a subject under examination;
   an imaging unit provided in the distal unit to image the subject under examination and output an electrical image signal;
   a light modulation device provided in the distal unit to output an optical image signal based on the electrical image signal output from the imaging unit;
   a first light cable inserted in the insertion unit to transmit light emitted by a communication light source provided outside the distal unit to the light modulation device;
   a second light cable inserted in the insertion unit to transmit the optical image signal output from the light modulation device outside the insertion unit;
   an endoscope user operation unit connected to the insertion unit; and
   a light source controller provided in the endoscope user operation unit to control an output of the communication light source,
   wherein:
   the communication light source is different from an illumination light source emitting an illumination light for illuminating the subject under examination,
   the light modulation device modulates the light transmitted by the first light cable to generate the optical image signal,
   the communication light source is provided in the endoscope user operation unit, and
   the light source controller controls the output of the communication light source based on a light emission intensity of the communication light source.

2. The endoscope according to claim 1, further comprising:
   a connection unit connectable to an image processing device, the image processing device being a device for processing the optical image signal,
   wherein:
   at least a portion of a set of the communication light source and the light source controller is provided in the connection unit, and
   the light source controller controls the output of the communication light source based on a light emission intensity of the communication light source.

3. The endoscope according to claim 2, wherein the light source controller controls the output of the communication light source based on a light intensity of the optical image signal transmitted by the second light cable.

4. The endoscope according to claim 2, further comprising:
   a third light cable inserted in the insertion unit to transmit the optical image signal output from the light modulation device to the light source controller,
   wherein:
   the optical image signal transmitted by the second light cable is transmitted outside the endoscope, and
   the light source controller controls the output of the communication light source in accordance with a light intensity of the optical image signal transmitted by the third light cable.

5. The endoscope according to claim 1, wherein the light source controller controls the output of the communication light source based on a light intensity of the optical image signal transmitted by the second light cable.

6. The endoscope according to claim 5, further comprising:
   a light splitter that branches a transmission channel of the optical image signal,
   wherein the light source controller includes a sensing unit for sensing the light intensity of the optical image signal branched by the light splitter and controls the output of the communication light source in accordance with a value sensed by the sensing unit.

7. The endoscope according to claim 6, wherein the light splitter and the light source controller are arranged on a same substrate and provided in the endoscope user operation unit.

8. The endoscope according to claim 1, further comprising:
a third light cable inserted in the insertion unit to transmit the optical image signal output from the light modulation device to the light source controller,
wherein:
the optical image signal transmitted by the second light cable is transmitted outside the endoscope, and
the light source controller controls the output of the communication light source in accordance with a light intensity of the optical image signal transmitted by the third light cable.

9. The endoscope according to claim 1, wherein:
the communication light source comprises a semiconductor laser, and
each of the first light cable and the second light cable comprises a single mode optical fiber.

10. The endoscope according to claim 1, wherein:
the light modulation device comprises a plurality of light modulation devices, and
the second light cable comprises a multicore fiber capable of transmitting optical image signals output from the plurality of light modulation devices.

11. The endoscope according to claim 1, wherein the communication light source emits one or a plurality of single-wavelength light beams.

12. The endoscope according to claim 1, further comprising:
a connection unit connectable to an image processing device, the image processing device being a device for processing the optical image signal,
wherein:
the second light cable is inserted in the connection unit, and
the second light cable has a convex-shaped fiber outgoing end from which the optical image signal outgoes.

13. The endoscope according to claim 1, wherein the communication light source emits light included in a wavelength band of 1200 nm-1400 nm.

14. An endoscopic system comprising an endoscope and an image processing device for processing an optical image signal from the endoscope, wherein the endoscope includes:
an insertion unit including a distal unit oriented toward a subject under examination;
an imaging unit provided in the distal unit to image the subject under examination and output an electrical image signal;
a light modulation device provided in the distal unit to output an optical image signal based on the electrical image signal output from the imaging unit;
a first light cable inserted in the insertion unit to transmit light emitted by a communication light source provided outside the distal unit to the light modulation device;
a second light cable inserted in the insertion unit to transmit the optical image signal output from the light modulation device outside the insertion unit; and
a light source controller provided in the image processing device to control an output of the communication light source,
wherein:
the communication light source is provided in the image processing device, and is different from an illumination light source emitting an illumination light for illuminating the subject under examination,
the light modulation device modulates the light transmitted by the first light cable to generate the optical image signal,
the image processing device generates an image capturing the subject under examination by demodulating the optical image signal transmitted by the second light cable, and
the light source controller controls the output of the communication light source based on a light emission intensity of the communication light source.

15. The endoscopic system according to claim 14, wherein the light source controller controls the output of the communication light source based on a light intensity of the optical image signal transmitted by the second light cable.

16. An endoscopic system comprising an endoscope and an image processing device for processing an optical image signal from the endoscope, wherein the endoscope includes:
an insertion unit including a distal unit oriented toward a subject under examination;
an imaging unit provided in the distal unit to image the subject under examination and output an electrical image signal;
a light modulation device provided in the distal unit to output an optical image signal based on the electrical image signal output from the imaging unit;
a first light cable inserted in the insertion unit to transmit light emitted by a communication light source provided outside the distal unit to the light modulation device;
a second light cable inserted in the insertion unit to transmit the optical image signal output from the light modulation device outside the insertion unit; and
a connection unit connectable to the image processing device,
wherein:
the communication light source is different from an illumination light source emitting an illumination light for illuminating the subject under examination,
the light modulation device modulates the light transmitted by the first light cable to generate the optical image signal,
the image processing device generates an image capturing the subject under examination by demodulating the optical image signal transmitted by the second light cable,
the image processing device further includes a photoelectric converter for converting the optical image signal into an electrical image signal, and a light transmission cable for transmitting the optical image signal transmitted by the second light cable to the photoelectric converter, and
the light transmission cable has a convex-shaped fiber outgoing end from which the optical image signal outgoes toward the photoelectric converter.

* * * * *